US00PP15107P3

(12) United States Plant Patent
Utecht

(10) Patent No.: US PP15,107 P2
(45) Date of Patent: Aug. 24, 2004

(54) GERANIUM PLANT NAMED 'FIP 202'

(50) Latin Name: *Pelargonium zonale L'Héritier×Pelargonium peltatum*
Varietal Denomination: Fip 202

(76) Inventor: Angelika Utecht, Hinterer Rebstock 38, 56410 Montabaur (DE)

( * ) Notice: Subject to any disclaimer, the term of this patent is extended or adjusted under 35 U.S.C. 154(b) by 0 days.

(21) Appl. No.: 10/715,541

(22) Filed: Nov. 19, 2003

(65) Prior Publication Data

US 2004/0073983 P1 Apr. 15, 2004

(30) Foreign Application Priority Data

Dec. 19, 2002 (CA) ..... PBR 02-3400

(51) Int. Cl.[7] ..... A01H 5/00

(52) U.S. Cl. ..... Plt./324
(58) Field of Search ..... Plt./324

(56) References Cited

PUBLICATIONS

GTITM UPOVROM Citation for 'Fip 202' as per DE PBR PEL 01641; Jun. 26, 2000.*

* cited by examiner

*Primary Examiner*—Kent Bell

(57) ABSTRACT

A new and distinct cultivar of geranium plant named 'Fip 202', and particularly characterized by the combined features of orange-red, double flowers, numerous, relatively small inflorescences, dark-green, zoned foliage with mostly round, only moderately large leaves, wide and bushy, moderately tall plant habit, somewhat late flowering, good tolerance of rain and heat, so all in all a robust plant for outdoor conditions, landscaping.

1 Drawing Sheet

Genus and species of the plant claimed: *Pelargonium zonale L'Héritier×Pelargonium peltatum.*
Variety denomination: 'Fip 202'.

BACKGROUND OF THE INVENTION

The present invention comprises a new and distinct cultivar of geranium, botanically known as hybrid Pelargonium, and hereinafter referred to by the cultivar name 'Fip 202'.

'Fip 202' is a product of a planned breeding program which had the objective of creating new hybrid geranium cultivars with red flower color, and vigorous, but well-branched growth habit.

'Fip 202' originated from a hybridization made by the inventor, Angelika Utecht, in a controlled breeding program in Hillscheid, Germany, in 1997. The female parent was an unpatented hybrid geranium plant, no. 90-2022-8, having red single-type flowers, dark-green foliage with strong zonation and fairly vigorous growth. The male parent of 'Fip 202' was the unpatented ivy geranium seedling no. 95-337-18, having salmon-red, double flowers, medium green leaves without zonation, and medium to strong growth habit.

'Fip 202' was selected as one flowering plant within the progeny of the stated cross by Angelika Utecht in 1998 in a controlled environment in Moncarapacho, Portugal.

The first act of asexual reproduction of 'Fip 202' was accomplished when vegetative cuttings were taken from the initial selection in the fall of 1998, in a controlled environment in Moncarapacho, Portugal, by, or under the supervision of, Angelika Utecht.

Horticultural examination of plants grown from cuttings of the plant initiated in May 1999, in Hillscheid, Federal Republic of Germany, and continuing thereafter, has demonstrated that the combination of characteristics as herein disclosed for 'Fip 202' are firmly fixed and are retained through successive generations of asexual reproduction.

'Fip 202' has not been observed under all possible environmental conditions. The phenotype may vary significantly with variations in environment such as temperature, light intensity and day length.

The following observations, measurements, and comparisons describe plants grown in Hillscheid, Germany, under greenhouse conditions which approximate those generally used in commercial practice.

BRIEF SUMMARY OF THE INVENTION

The following traits have been repeatedly observed and are determined to be basic characteristics of 'Fip 202' in combination distinguish this geranium as a new and distinct cultivar:

1. Orange-red, medium sized flowers;
2. Numerous, compact, semi-spherically shaped inflorescences;
3. Dark-green foliage with strong zonation;
4. Bushy, mostly round, little spreading or overhanging plant habit;
5. Relatively late flowering response, but floriferous;
6. Good tolerance to rain and heat; and
7. Suitable as a robust plant for landscaping, requiring little care.

Of the many commercial cultivars known to the present inventor, the most similar in comparison to 'Fip 202' is the patented variety 'Fisgren' (U.S. Plant Pat. No. 12,451).

In comparison to 'Fisgren', 'Fip 202' a somewhat different flower color, much more petals per corolla, smaller and darker green leaves, shorter and deeper red colored peduncles, and more compact plant habit.

BRIEF DESCRIPTION OF THE DRAWING

The accompanying photographic drawing shows typical flower and foliage characteristics of 'Fip 202' with colors being as true as possible with an illustration of this type.

The photographic drawing shows a 'Fip 202' plant in a hanging basket.

DETAILED BOTANICAL DESCRIPTION

The measurements were taken in Hillscheid, Germany, in mid May, 12 weeks after planting of rooted cuttings. The plants were growing in 14 cm pots, they had not been pinched.

In the following description color references are made to The Royal Horticultural Society Colour Chart. The color values were determined indoors from plants growing in a greenhouse in May 2003, in Hillscheid, Germany.

INFLORESCENCE

Umbel:

*Shape.*—Semi-spherical, tight.
*Average diameter.*—91 mm.
*Average depth.*—45 mm.
*Peduncle length.*—139 mm.
*Peduncle color.*—Partly green, RHS 137 D, mainly reddish brown, RHS 184 A.
*Pedicel.*—28 mm in length, spur occasionally visible just below the flower.
*Pedicel color.*—Dark brown, RHS 183 C.
*Number of flowers per umbel.*—Approximately 20–30.

Corolla:

*Average diameter.*—46 mm.
*Depth.*—Approximately 12 mm.
*Form.*—Double.
*Shape.*—Round outline, many petals arranged horizontally to nearly vertically.
*Number of petals.*—20–25.
*Shape of petals.*—Obovate, base acute, upper end is truncate or rounded, margin is entire or very weakly crenated.
*Size of petals.*—Upper petals: 20 mm long, 11 mm wide; lower petals: 18–20 mm long, 12 mm wide.
*Color (general tonality from a distance of three meters).*—Orange red, uniform.
*Color of upper petals.*—Main part RHS 43 A.
*Markings of upper petals.*—Two dark veins, RHS 187 D, weak, most often not visible, as covered by inner petals.
*Color of lower petals.*—RHS 43 A.
*Markings of lower petals.*—None.
*Color of lower surface of petals.*—RHS 41 A, relatively uniform.
*Color of sepals.*—Outer surface: light green, RHS 144 A; inner surface: light green, RHS 144 B.
*Number of sepals.*—5, occasionally an incomplete $6^{th}$ can be found.
*Shape of sepals.*—Linear to lanceolate, acute tip, base sessile, surface with weak pubescence, margin entire.
*Size of sepals.*—7–8 mm long, 4 mm wide for the largest upper sepal, 2 mm in width for the other sepals.

Bud: (just prior to petals unfolding).

*Shape.*—Wide elliptical to nearly round.
*Color of sepals.*—Light green, RHS 143 C.
*Color of petals.*—RHS 43 A.
*Length.*—17–18 mm.
*Width.*—10–13 mm.

REPRODUCTIVE ORGANS

*Androecium.*—2–5 fertile anthers, moderate pollen, yellow-orange, RHS 28 A, lower side of anthers blackish, RHS 187 A, filaments white, RHS 155 D, to light-pink, RHS 52 D.
*Gynoecium.*—One pistil, style whitish, stigma RHS 42 A, 5–6-lobed.
*Fertility/seed set.*—No seed set observed.

Spring flowering response period: In Hillscheid, Germany, in 2001 plants had on average 0.2 flowers opened 9 weeks after planting of rooted cuttings.

Outdoor flower production: Continuously and rich flowering, the flower count in 2003 in Hillscheid, Germany, indicated only about 1–2 inflorescence per plant in mid May, but later up to 14 inflorescences per plant.

Durability: Good stability of flower color, no fading, good heat tolerance, good rain resistance.

Lastingness of the individual flower: About 8 days at 18° C., about 15 days for the umbel.

Fragrance: None.

PLANT

Foliage:

*Shape.*—Nearly round, with cordate base, with the gap between the lowest lobes mostly closed, apex with weak lobes, which are somewhat stronger than those of *Pelargonium zonale* varieties known to the inventor, but much weaker than those of most *Pelargonium peltatum* varieties known to the inventor.
*Margin.*—Bicrenated.
*Texture.*—Upper surface smooth, dull.
*Size of leaf.*—About 80 mm wide, 45 mm long.
*Color of upper surface.*—Dark-green, approximately RHS 137 A.
*Zonation.*—Relatively narrow, brown, about RHS 166 A.
*Color of lower surface.*—RHS 137 C to RHS 137 D.
*Petioles.*—60–65 mm long, 3 mm diameter, green in color, approximately RHS 137 C.

General appearance and form:

*Stem color.*—Green, RHS 137 D, partly reddish-brown, RHS 184 A.
*Internode length.*—10–5 mm.
*Branching pattern.*—7–10 branches.
*Size of plants.*—Height 24.5 cm, 27.1 cm wide (12-week-old plants, as described), measured from the top of the soil (base of the main stem) to the surface of the foliage canopy, without inflorescences.

Plant habit: The plant habit of 'Fip 202' is closer to that of zonal geranium varieties than to ivy geranium varieties. When planted in tubs it develops mainly into a bushy, rounded and wide plant, only when growing very tall the branches may be overhanging.

I claim:

1. A new and distinct cultivar of geranium plant named 'Fip 202', as described and illustrated herein.

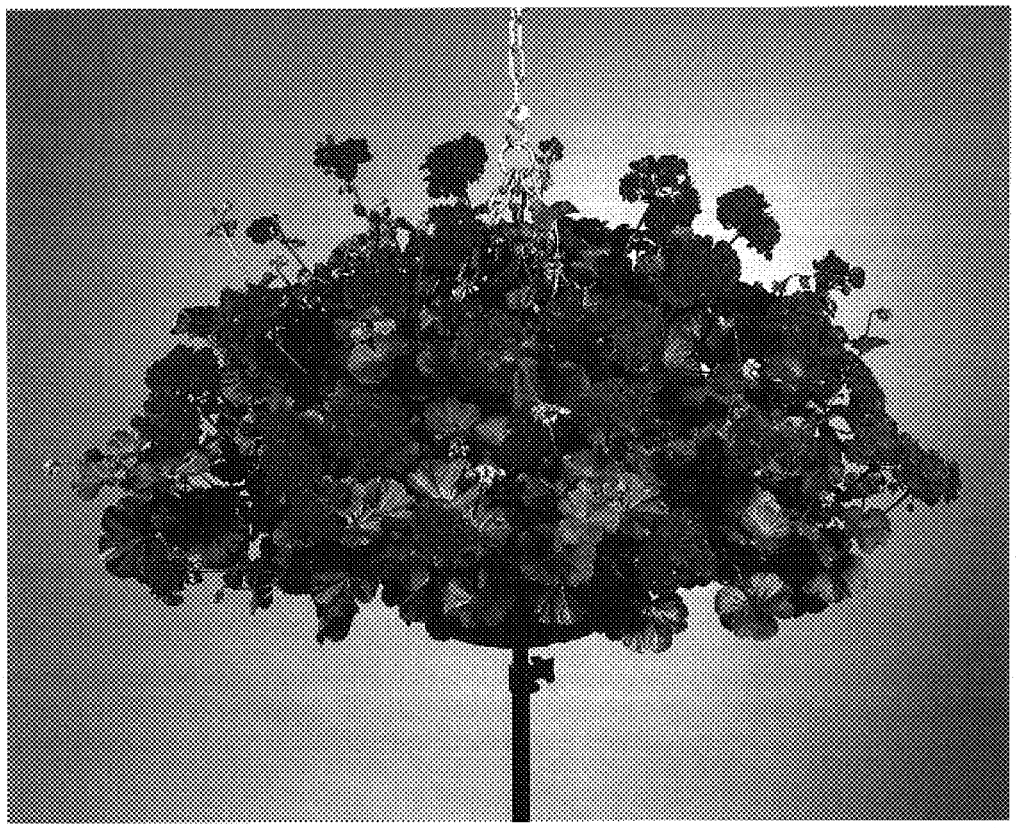

* * * * *